United States Patent
Csutak

(10) Patent No.: US 8,487,238 B2
(45) Date of Patent: Jul. 16, 2013

(54) METHOD OF IDENTIFICATION OF PETROLEUM COMPOUNDS USING FREQUENCY MIXING ON SURFACES

(75) Inventor: Sebastian Csutak, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 777 days.

(21) Appl. No.: 12/632,147

(22) Filed: Dec. 7, 2009

(65) Prior Publication Data

US 2010/0148049 A1 Jun. 17, 2010

Related U.S. Application Data

(63) Continuation-in-part of application No. 11/933,538, filed on Nov. 1, 2007, now abandoned.

(51) Int. Cl.
*G01V 3/18* (2006.01)
*G01N 21/63* (2006.01)

(52) U.S. Cl.
USPC ........... 250/254; 250/339.06; 324/333; 702/6

(58) Field of Classification Search
USPC 250/253, 254, 256, 262, 269.1, 336.1; 702/6; 324/333
See application file for complete search history.

(56) References Cited

U.S. PATENT DOCUMENTS

| | | | |
|---|---|---|---|
| 4,994,671 A | 2/1991 | Safinya et al. | |
| 5,262,644 A | 11/1993 | Maguire | |
| RE36,799 E | 8/2000 | Nishi | |
| 6,111,640 A | 8/2000 | Hedman et al. | |
| 6,437,326 B1 | 8/2002 | Yamate et al. | |
| 6,465,775 B2 | 10/2002 | Mullins et al. | |
| 6,707,556 B2 | 3/2004 | Turner et al. | |
| 7,218,655 B2 | 5/2007 | Wang et al. | |
| 2001/0010747 A1 | 8/2001 | Dourdeville et al. | |
| 2002/0043620 A1 | 4/2002 | Tchakarov et al. | |
| 2002/0154309 A1 | 10/2002 | Walker et al. | |
| 2002/0163636 A1 | 11/2002 | Oberleitner et al. | |
| 2003/0011774 A1 | 1/2003 | DiBello et al. | |
| 2003/0056581 A1 | 3/2003 | Turner et al. | |
| 2003/0058450 A1 | 3/2003 | Mosley et al. | |
| 2003/0062472 A1 | 4/2003 | Mullins et al. | |

(Continued)

OTHER PUBLICATIONS

Baldelli et al., "Surface enhanced sum frequency generation of carbon monoxide adsorbed on platinum nanoparticle arrays," Journal of Chemical Physics, vol. 113, No. 13, Published Oct. 1, 2000, pp. 5432-5438, Retrieved from internet [Aug. 2, 2012]. Retrieved from url <http://jcp.aip.org/resource/1/jcpsa6/v113/i13/p5432_s1>.*

(Continued)

*Primary Examiner* — David Porta
*Assistant Examiner* — Jeremy Valentiner
(74) *Attorney, Agent, or Firm* — Cantor Colburn LLP

(57) ABSTRACT

A method for estimating a chemical composition of a material in a borehole penetrating the earth, the method includes: placing an analysis unit into the borehole; placing a sample of the material onto an enhanced surface of the analysis unit, the enhanced surface having a feature configured to increase an electric susceptibility of the sample at an interface between the sample and the enhanced surface; illuminating the sample at the interface with a first light beam and a second light beam; measuring sum frequency light generated from the illuminating; and analyzing the sum frequency light to estimate the chemical composition of the material.

22 Claims, 7 Drawing Sheets

U.S. PATENT DOCUMENTS

| | | |
|---|---|---|
| 2003/0072000 A1 | 4/2003 | Pfeifer et al. |
| 2003/0072514 A1 | 4/2003 | Ames |
| 2003/0076500 A1 | 4/2003 | Nanami et al. |
| 2003/0086091 A1 | 5/2003 | Hinnrichs et al. |
| 2003/0095259 A1 | 5/2003 | Luryi et al. |
| 2003/0106993 A1 | 6/2003 | Chen et al. |
| 2003/0160164 A1 | 8/2003 | Jones et al. |
| 2004/0007665 A1 | 1/2004 | DiFoggio et al. |
| 2004/0033017 A1 | 2/2004 | Kringlebotn et al. |
| 2004/0069942 A1 | 4/2004 | Fujisawa et al. |
| 2004/0129874 A1 | 7/2004 | Torgersen et al. |
| 2004/0164237 A1 | 8/2004 | Jones et al. |
| 2004/0178336 A1 | 9/2004 | DiFoggio |
| 2004/0207913 A1 | 10/2004 | Mehuys et al. |
| 2004/0233452 A1 | 11/2004 | Prelewitz |
| 2004/0252748 A1 | 12/2004 | Gleitman |
| 2004/0263851 A1 | 12/2004 | Dobbs et al. |
| 2005/0030540 A1 | 2/2005 | Thornton |
| 2005/0036146 A1 | 2/2005 | Braig et al. |
| 2005/0068536 A1 | 3/2005 | Schwabe |
| 2005/0111003 A1 | 5/2005 | Kawasaki |
| 2005/0122520 A1 | 6/2005 | Yan |
| 2005/0200851 A1 | 9/2005 | Kojima |
| 2006/0012784 A1 | 1/2006 | Ulmer |
| 2006/0012793 A1 | 1/2006 | Harris |
| 2006/0017930 A1 | 1/2006 | Canty et al. |
| 2006/0050279 A1 | 3/2006 | Kurozumi et al. |
| 2006/0103846 A1 | 5/2006 | Pages Pinyol |
| 2006/0109469 A1 | 5/2006 | Schleifer |
| 2006/0132901 A1* | 6/2006 | Miller ............................. 359/326 |
| 2006/0139646 A1 | 6/2006 | DiFoggio |
| 2006/0152730 A1 | 7/2006 | Schneider |
| 2006/0163476 A1 | 7/2006 | Huang et al. |
| 2006/0176486 A1 | 8/2006 | Ho |
| 2006/0232779 A1 | 10/2006 | Shaw |
| 2006/0268276 A1 | 11/2006 | Tajima |
| 2007/0002309 A1 | 1/2007 | Yamamoto |
| 2007/0013911 A1 | 1/2007 | DiFoggio |
| 2007/0035737 A1 | 2/2007 | Andrews et al. |
| 2007/0053671 A1 | 3/2007 | Garg et al. |
| 2007/0120051 A1 | 5/2007 | DiFoggio et al. |
| 2007/0153282 A1 | 7/2007 | Zubkov et al. |
| 2007/0188763 A1 | 8/2007 | Schenki |
| 2007/0229830 A1 | 10/2007 | Yamamoto et al. |
| 2008/0149819 A1 | 6/2008 | Zhdaneev |
| 2008/0165356 A1 | 7/2008 | DiFoggio et al. |
| 2008/0277595 A1 | 11/2008 | Lundquist et al. |

OTHER PUBLICATIONS

Guo et al., "Linear and nonlinear optical properties of carbon nanotubes from first-principles calculations," Physical Review B, vol. 69, pp. 205416-1-205416-11, published 2004. Retrieved from internet [Aug. 12, 2012]. Retrieved from url <http://prb.aps.org/abstract/PRB/v69/i20/e205416>.*

Allen, et al. "Non-linear vibrational sum frequency spectroscopy of atmospherically relevant molecules at aqueous solution surfaces", Current Opinion in Colloid & Interface Science 5 (2000) 74-80.

Bain, Colin, "Faraday research Article: Sum-frequency Vibrational Spectroscopy of the Solid/Liquid Interface"; Journal of Chemical Society, Faraday Trans. vol. 91(9), 1995, pp. 1281-1296.

Bernath, Peter, "Chapter 7: Infrared Laser Spectroscopy of Transient Species" Retrived online {Sep. 24, 2008]. Published Nov. 9, 2001. retrived from URL <http://bernath.uwaterloo.ca/media/IRLaserREv.pdf>.

D.L. Mills, 8. Nonlinear Optical Interactions at Surfaces and Interfaces, Nonlinear Optics, Basic Concepts. Second, Enlarged Edition. pp. 156-190.

DeSimone, "Surface specificity of sum frequency spectroscopy". Journal of Chemistry 571, vol. 1, No. 1. Dec. 28, 2005. pp. 1-5.

Hommel, et al. "Broadband Vibrational Sum Frequency Generation Spectroscopy of a Liquid Surface". Analytical Sciences, Nov. 2001, Vo. 17. pp. 1325-1329.

Sum Frequency Generation in Vibrational Spectroscopy. Iowa State University, Ames, IA 50010. pp. 1-16.

G.H. Dieke, et al., "The Spectra of the Doubly and Triply Ionized Rare Earths," Applied Optics, Jul. 1963, pp. 675-686, vol. 2, No. 7.

R.M. Percival, et al. "Thulium-Doped Monomode Fluoride Fibre Laser Broadly Tunable from 2.25 to 2.5 μm," Electronics Letters, Oct. 10, 1991, pp. 1912-1913, vol. 27, No. 21.

R.M. Percival, et al. "Highly Efficient and Tunable Operation of Two Colour Tm-Doped Fluoride Fibre Laser", Electronics Letter, Mar. 26, 1992, pp. 671-673, vol. 28, No. 7.

R.M. Percival, et al. "Highly Efficient CW Cascade Operation of 1-47 and 1-82 μm Transitions in Tm-Doped Fluoride Fiber Laser," Electronics Letters, Sep. 24, 1992, pp. 1866-1868, vol. 28. No. 20.

R.M. Percival, et al., "Thulium Sensitised Holmium-Doped CW Fluoride Fibre Laser of High Efficiency", Electronics Letters, No. 19, 1992, pp. 2231-2232, vol. 28, No. 24.

F.J. Mcaleavey, et al., "Efficient Diode Pumped Tm3+–Doped Fluoride Fibre Laser of Hydrocarbon Gas Sensing", Electronics Letters, May 11, 1995, pp. 800-802, vol. 31, No. 10.

R. Paschotta, et al., "Efficient Superfluorescent Light Sources with Broad Bandwidth," IEEE Journal of Selected Topics in Quantum Electronics, Aug. 1997, pp. 1097-1099, vol. 3, No. 4.

F.J. Mcaleavey, et al. "Narrow Linewidth, Tubable Tm3+–Doped Fluoride Fiber Laser for Hydrocarbon Gas Sensing, "IEEE Journal of Selected Topics in Quantum Electronics, Aug. 1997, pp. 1103-1111, vol. 3. No. 4.

T. Sondergaard, "Photonic Crystal Distributed Feedback Fiber Lasers with Bragg Gratings," Apr. 2000, pp. 589-597, vol. 18, No. 4.

S.J. Mihailov, et al "Bragg Gratings Written in All-SiO2 and Ge-Doped core Fibers with 800-nm Femtosecond Radiation and a Phase Mask," Jan. 2004, pp. 94-100, vol. 22, No. 1.

I. Bennion, et al., "Fiber Bragg Grating Technologies and Applications in Sensors," Optical Fiber communication Conference and Exposition, Mar. 10, 2006.

S.D. Jackson, "Midinfrared Holmium Fiber Lasers," IEEE Journal of Quantum Electronics, Feb. 2006, pp. 187-191, vol. 42, No. 2.

D. Grobnic, et al. "Long-term Thermal Stability Tests at 1000C of Silica Fibre Bragg Gratings Made with Ultrafast Laser Radiation," Apr. 7, 2006, pp. 1009-1013.

A. Martinez, et al., "Direct Inscription of Bragg Gratings in Coated Fibers by an Infrared Femtosecond Laser", Optics Letters, Jun. 1, 2006, pp. 1603-1605, vol. 31, No. 11.

Y. Lai et al, "Distributed Bragg reflector Fiber Laser Fabricated by Femtosecond Laser Inscription," Optics Letters, Jun. 1, 2006, pp. 1672-1674, vol. 31, No. 11.

JDS Uniphase Corporation, "High-Speed, High-Temperature Data Link Diode Lasers: 5800 Series," Product Brochure, 2006.

Nufern, "Eye Safe 25/250 Thulium-Doped Double Clad Fiber," Product Brochure, Nov. 2006.

Bookham, Inc., "980nm Pump Laser Module, Uncooled LU9**X," Product Brochure, Jan. 2007.

R. Paschotta, "Rare-earth-doped Fibers," Encyclopedia of Laser Physics and Technology, Mar. 10, 2007, available from http://www.rp-photonics.com/rare_earth_doped_fibers.html.

* cited by examiner

METHOD OF IDENTIFICATION OF PETROLEUM COMPOUNDS USING FREQUENCY MIXING ON SURFACES

CROSS REFERENCE TO RELATED APPLICATIONS

This application is a Continuation In Part of U.S. Non Provisional application Ser. No. 11/933,538 filed Nov. 1, 2007, the entire disclosure of which is incorporated herein by reference.

BACKGROUND OF THE INVENTION

1. Field of the Invention

The invention disclosed herein relates to identifying the chemical composition of a material that is located in a borehole. In particular, analysis of the material is performed within the borehole.

2. Description of the Related Art

A variety of geologic formations contain reservoirs of petroleum. Measuring properties of the geologic formations provides information that can be useful for locating the reservoirs of petroleum. In addition, it is important to monitor the reservoirs that are already located. Monitoring provides information useful for optimizing production resources.

Generally, petroleum is accessed by drilling a borehole into the subsurface of the earth. The borehole also provides access for taking samples of materials from the borehole. The samples may be taken to the surface of the earth for analysis in a chemistry laboratory. The analysis is used to determine a chemical composition of a material in the borehole such as a petroleum compound. There are a few disadvantages to analyzing the samples in the laboratory. One disadvantage is that transporting the samples to the laboratory can be time consuming. Another disadvantage is that while samples are being withdrawn from the borehole other uses of the borehole may be precluded. One technique that can overcome these disadvantages is well logging.

Well logging is a technique used to take measurements of the geologic formations and reservoirs from the borehole. In one embodiment, a logging instrument is lowered on the end of a wireline into the borehole. The logging instrument sends data via the wireline to the surface for recording. Output from the logging instrument comes in various forms and may be referred to as a "log."

Therefore, what are needed are techniques for logging the chemical composition of a material in a borehole.

BRIEF SUMMARY OF THE INVENTION

Disclosed is one example of a method for estimating a chemical composition of a material in a borehole penetrating the earth, the method includes: placing an analysis unit into the borehole; placing a sample of the material onto an enhanced surface of the analysis unit, the enhanced surface having a feature configured to increase an electric susceptibility of the sample at an interface between the sample and the enhanced surface; illuminating the sample at the interface with a first light beam and a second light beam; measuring sum frequency light generated from the illuminating; and analyzing the sum frequency light to estimate the chemical composition of the material.

Also disclosed is an embodiment of a computer-readable medium comprising machine-executable instructions for estimating a chemical composition of a material in a borehole penetrating the earth by performing a method including: placing an analysis unit into the borehole; placing a sample of the material onto an enhanced surface of the analysis unit, the enhanced surface having a feature configured to increase an electric susceptibility of the sample at an interface between the sample and the enhanced surface; illuminating the sample at the interface with a first light beam and a second light beam; measuring sum frequency light generated from the illuminating; and analyzing the sum frequency light to estimate the chemical composition of the material.

Further disclosed is an embodiment of an apparatus for estimating a chemical composition of a material in a borehole penetrating the earth, the apparatus includes: a carrier; and an analysis unit disposed at the carrier, the analysis unit having an enhanced surface, at least a first light source and a second light source, and a light detector, the enhanced surface having a feature configured to increase an electric susceptibility of the sample at an interface between the sample and the enhanced surface; wherein the analysis unit is configured to receive a sample of the material from a downhole environment onto the enhanced surface, illuminate the material at the interface with the light sources, and measure a characteristic of sum frequency light generated from the illumination with the light detector to estimate the chemical composition.

BRIEF DESCRIPTION OF THE DRAWINGS

The subject matter, which is regarded as the invention, is particularly pointed out and distinctly claimed in the claims at the conclusion of the specification. The foregoing and other features and advantages of the invention are apparent from the following detailed description taken in conjunction with the accompanying drawings, wherein like elements are numbered alike, in which:

DETAILED DESCRIPTION OF THE INVENTION

Figure 1:
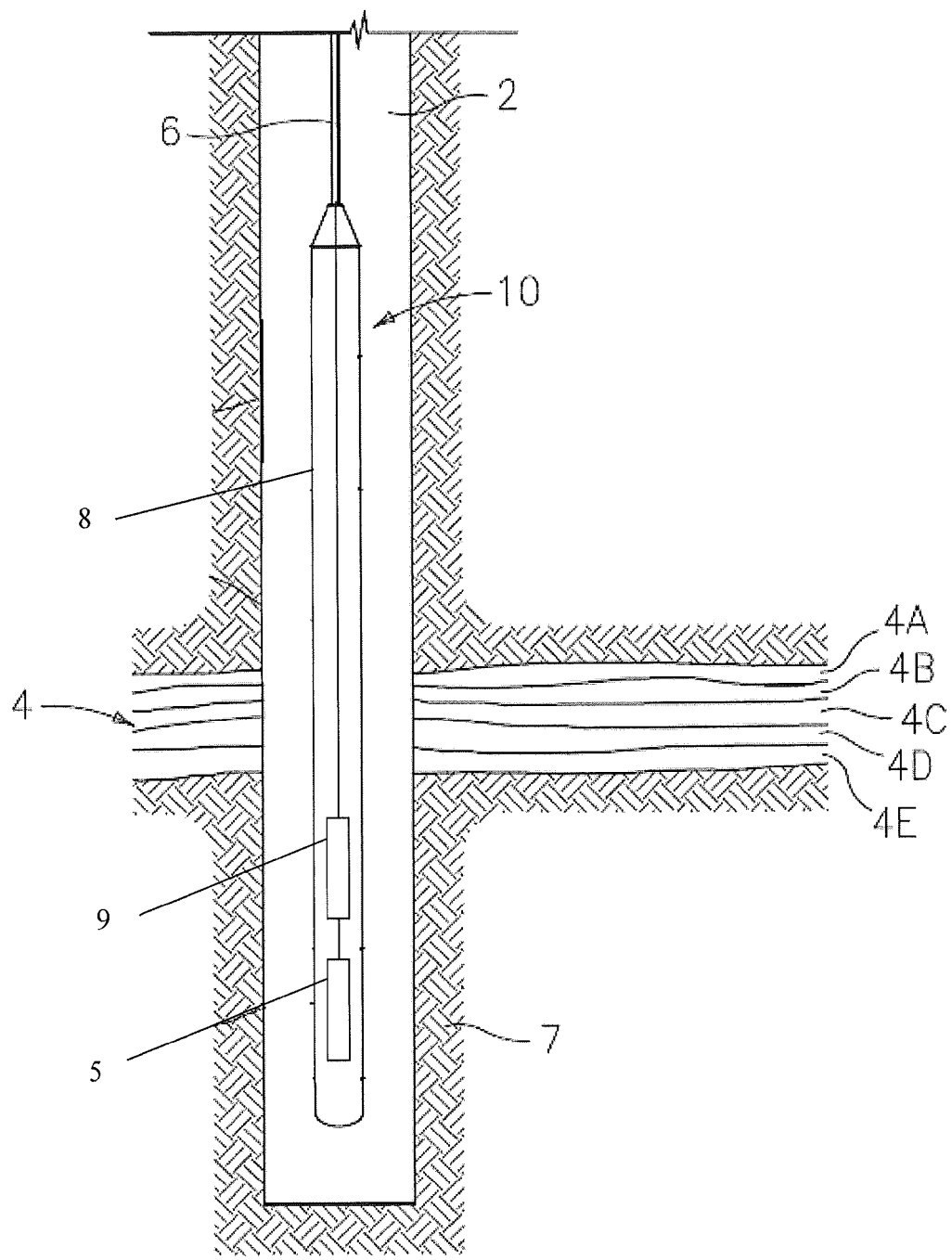
FIG. 1 illustrates an exemplary embodiment of a logging instrument in a borehole penetrating the earth.

The teachings provide techniques for accurately performing a chemical analysis of a material located within a borehole. A petroleum compound located in a reservoir can be identified using these techniques.

The techniques include an analysis unit for performing the chemical analysis. The analysis unit is placed in the borehole with a logging instrument to perform the chemical analysis. The analysis unit uses spectroscopy to analyze materials located within the borehole. In particular, the analysis unit performs sum frequency spectroscopy on a layer of material adsorbed to a metal surface.

Sum frequency spectroscopy is an optical technique that analyzes a material at an interface between the material and the metal surface. In sum frequency spectroscopy, two light beams, a first light beam and a second light beam, are directed at the interface. The angle each light beam makes with respect to the interface is generally not ninety degrees. The first light beam and the second light beam are directed so that the two light beams will overlap each other in space and time at the interface. One of the light beams has a frequency generally in the infrared region of the light spectrum. The other light beam has a frequency generally in the visible region of the light spectrum. Because of the overlap, an interaction between the first light beam and the second light beam will occur. From the interaction, a third light beam will be emitted from where the overlap occurs at the interface. The third light beam will have a frequency that is the sum of the frequencies of the first light beam and the second light beam. The angle that the third light beam makes with the interface is the angle required to conserve momentum. The third light beam is generated because a nonlinear optical phenomenon known as "sum frequency generation" or "three wave mixing." The third light beam is referred to as the "sum frequency light beam" or "sum frequency light."

The first light beam and the second light beam can be provided by lasers. In general, a laser providing the light beam in the infrared region is tunable while the laser providing the light beam in the visible region is fixed. When the frequency of the infrared laser is tuned, a frequency (resonant frequency) may be reached that is in resonance with a vibrational mode of the surface molecules of the material at the interface. At the resonant frequency, the intensity of the sum frequency beam is enhanced.

The sum frequency beam can be characterized by an intensity and a wavelength (or wavenumber). As the frequency of the light emitted from the infrared laser is varied, the intensity of the sum frequency beam can also vary. Plotting the intensity versus the wavelength for the sum frequency beam provides a "vibrational sum frequency (VSF) spectrum."

The intensity of the sum frequency beam $I(f_1+f_2)$ can be determined by equation (1)

$$I(f_1+f_2)=k|\chi^{(2)}_{eff}|^2 I(f_1) I(f_2) \quad (1)$$

where k represents a constant of proportionality, $\chi^{(2)}_{eff}$ represents the effective second order electric susceptibility of the material being analyzed, $I(f_1)$ represents the intensity of the first light beam at frequency $f_1$, and $I(f_2)$ represents the intensity of the second light beam at frequency $f_2$. Because of molecular symmetry in the interior of a material away from a boundary, the effective second order electric susceptibility of the material is about zero. However, the boundary at the interface breaks the molecular symmetry of the material with the result that the effective second order electric susceptibility at the interface is non-zero. The effective second order electric susceptibility at the interface is determined by the molecular structure of the material. The molecular structure of the material is unique to the chemistry of the material. Therefore, the VSF spectrum is unique to the chemistry of the material. By obtaining the VSF spectrum of the material, the chemical composition of the material can be identified.

The VSF spectrum for various materials expected in the borehole can be at least one of calculated and obtained by experiment. The VSF spectrum determined for a known material compound is referred to as "reference VSF spectrum." The VSF spectrum obtained from the analysis unit can be compared to reference VSF spectrums to determine the material compound producing the VSF spectrum.

For convenience, certain definitions are provided. The term "overlap" relates to the requirement that two light beams must generally occupy the same space at the same time in order to produce the sum frequency beam. The term "housing" relates to a structure of a logging instrument. The housing may used to at least one of contain and support the analysis unit.

Referring to FIG. 1, a well logging instrument 10 is shown disposed in a borehole 2. The logging instrument 10 may be used for measuring at least one of characteristics of a formation and borehole parameters. The logging instrument 10 includes an instrument housing 8 adapted for use in the borehole 2. The borehole 2 is drilled through earth 7 and penetrates formations 4, which include various formation layers 4A-4E. The logging instrument 10 is typically lowered into and withdrawn from the borehole 2 by use of an armored electrical cable 6 or similar conveyance as is known in the art. An analysis unit 5 is disposed in the housing 8 as shown in FIG. 1. Also shown disposed in the housing 8 is an electronic unit 9. The electronic unit 9 is used for at least one of processing and recording output from the analysis unit 5.

In some embodiments, the borehole 2 includes materials such as would be found in oil exploration, including a mixture of materials such as water, drilling fluid, mud, petroleum compounds and formation fluids that are indigenous to the various formations. One skilled in the art will recognize that the various features as may be encountered in a subsurface environment may be referred to as "formations." Accordingly, it should be considered that while the term "formation" generally refers to geologic formations of interest, that the term "formations," as used herein, may, in some instances, include any geologic points of interest (such as a survey area).

For the purposes of this discussion, it is assumed that the borehole 2 is vertical and that the formations 4 are horizontal. The teachings herein, however, can be applied equally well in deviated or horizontal wells or with the formation layers 4A-4E at any arbitrary angle. The teachings are equally suited for use in logging while drilling (LWD) applications and in open-borehole and cased-borehole wireline applications. In LWD applications, the logging instrument 10 may be disposed in a drilling collar. When used in LWD applications, drilling may be halted temporarily to prevent vibrations while the analysis unit 5 is used to perform a measurement.

Figure 2:
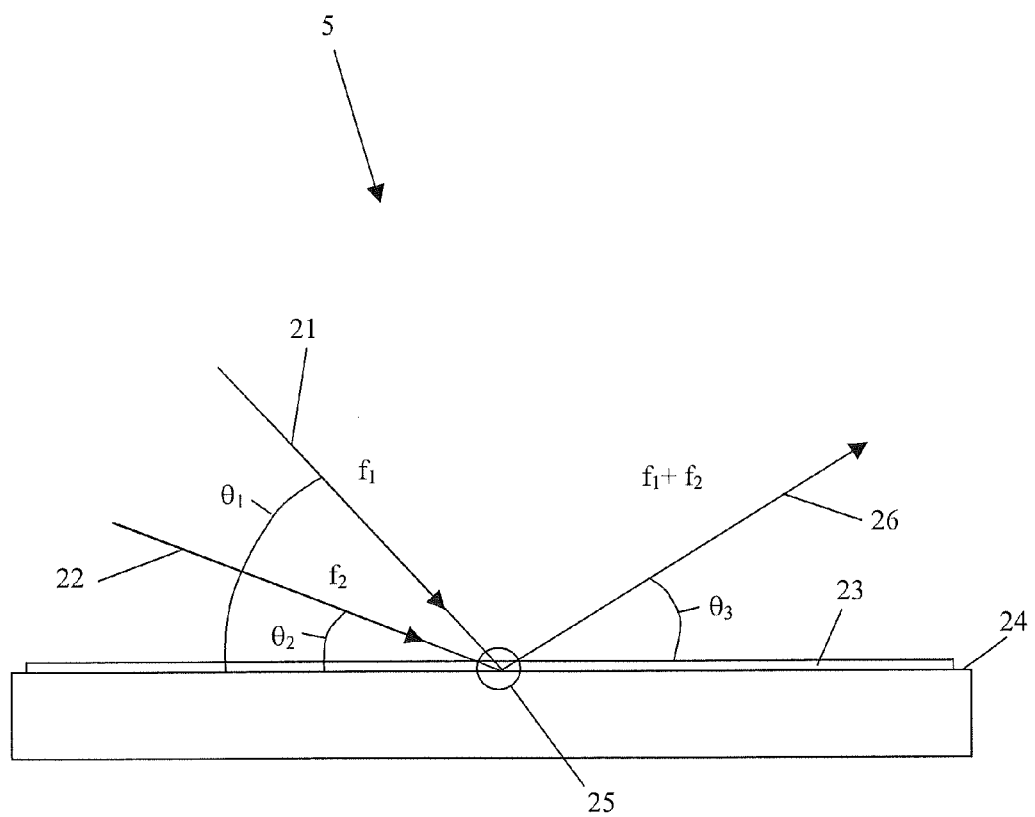
FIG. 2 illustrates aspects of an exemplary embodiment of an analysis unit for performing a chemical analysis.

FIG. 2 depicts aspects of one embodiment of the analysis unit 5. Referring to FIG. 2, the analysis unit 5 provides a first light beam 21 with a frequency $f_1$ and a second light beam 22 with a frequency $f_2$. For teaching purposes, the frequency $f_1$ is selected to be in the infrared region of the light spectrum. The first light beam 21 is tunable over a range of frequencies in the infrared region. The second light beam 22 has frequency $f_2$ fixed in the visible light spectrum. As shown in FIG. 2, a layer of material 23 is disposed upon a metal surface 24. Also depicted in FIG. 2 is an interface 25 where the material 23 is adsorbed to the metal surface 24. An exemplary embodiment of the metal surface 24 is a platinum surface.

Referring to FIG. 2, the first light beam 21 and the second light beam 22 are directed so as to overlap at the interface 25. The first light beam makes an angle $\theta_1$ with the metal surface 24. Similarly, the second light beam 22 makes an angle $\theta_2$ with the metal surface 24. In general, the angles $\theta_1$ and $\theta_2$ are not ninety degrees. The first light beam 21 interacts with the second light beam 22 at the interface 25 to produce a sum frequency light beam 26 with frequency $(f_1+f_2)$ and angle $\theta_3$. The sum frequency light beam 26 is reflected from the metal surface 24 at the interface 25. The intensity I3 of the sum frequency light beam 26 is proportional to the intensity I1 of the first light beam 21, the intensity of the second light beam 22, and the square of the second order electric susceptibility of the material 23. The second order electric susceptibility of the material 23 is a function of the frequencies $f_1$ and $f_2$ and, therefore, will vary as $f_1$ varies. The angle $\theta_3$ is the angle required to conserve momentum resulting from the three wave mixing.

Figure 3:
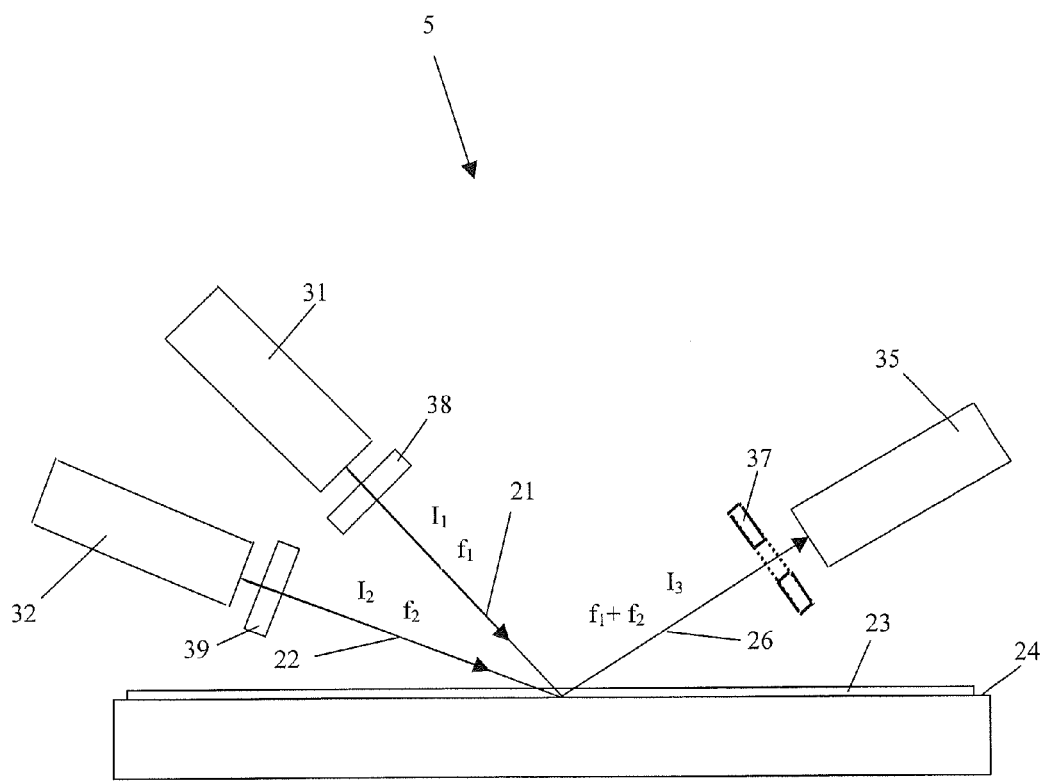
FIG. 3 illustrates an exemplary embodiment of the analysis unit for performing a chemical analysis.

FIG. 3 illustrates an exemplary embodiment of the analysis unit 5. Referring to FIG. 3, a first light source 31 provides the first light beam 21 while a second light source 32 provides the second light beam 22. An exemplary embodiment of each of the first light source 31 and the second light source 32 is a laser. To exclude undesired frequencies of light in the first light beam 21 and the second light beam 22, the first light source 31 and the second light source 32 may each include an optical filter. In the embodiment of FIG. 3, a first optical filter 38 is shown associated with the first light source 31. Similarly, a second optical 39 filter is shown associated with the second light source 32. Each optical filter may also be used to polarize light transmitted through the optical filter.

Referring to FIG. 3, a light detector 35 is depicted for measuring the intensity $I_3$ of the sum frequency light beam 26. Exemplary embodiments of the light detector 35 include at least one of a photomultiplier tube and a photodiode. In order to exclude any unwanted modes of light from entering the photodetector 35, an iris 37 is used to spatially filter light as shown in FIG. 3.

Figure 4:
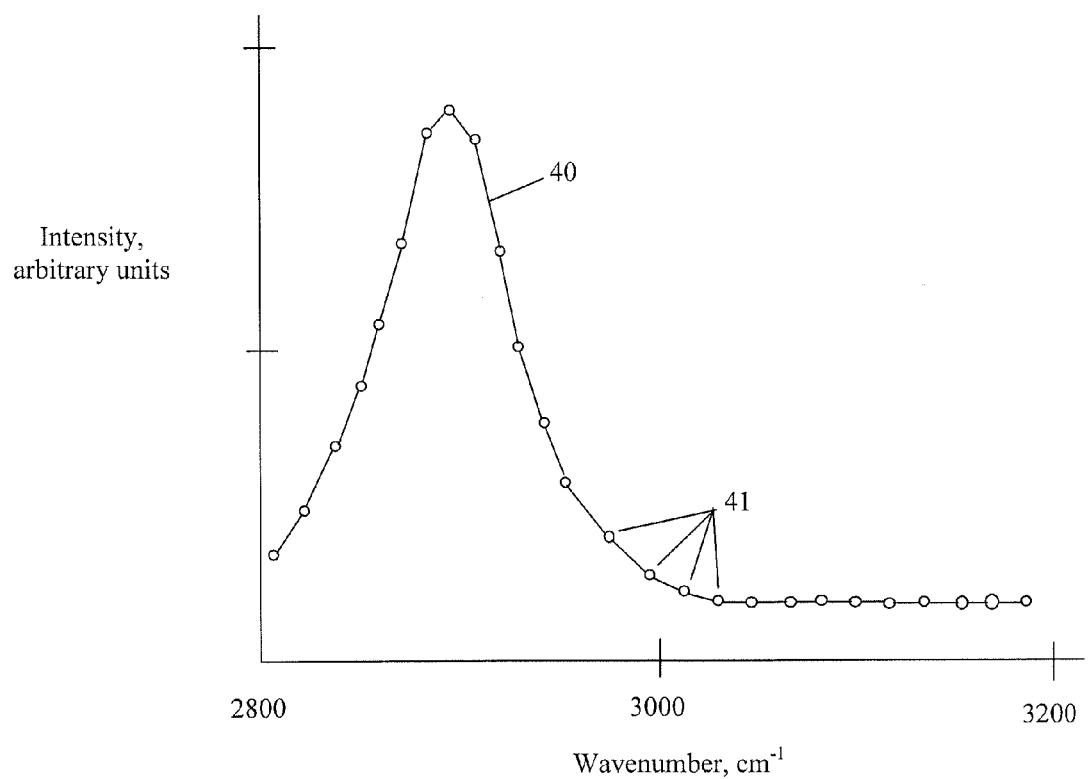
FIG. 4 is an exemplary plot of a vibrational sum frequency spectrum.

FIG. 4 is an exemplary plot of a VSF spectrum 40. In the plot of FIG. 4, twenty-six data points 41 are used to construct the VSF spectrum 40 for illustration purposes. Each of the data points 41 corresponds to the frequency $f_1$ (of the first light beam 21) that is varied in the infrared region. Increasing the number of data points 41 will increase the accuracy of the VSF spectrum 40.

An embodiment for analyzing a chemical composition of the material 23 in the borehole 2 may include a plurality of the analysis units 5. Each analysis unit 5 in the plurality can have components such as the first light source 31, the second light source 32, and the light detector 35 made with solid state technology. Using solid state fabrication, components in the analysis unit 5 can better survive the rigors of a borehole environment. In this embodiment, the frequency for each of the first light beam 21 and the second light beam 22 is fixed. Because the frequency of each light beam is fixed, the number of analysis units 5 in the plurality must be equal to or greater than the number of data points 41 desired to plot the VSF spectrum. For example, if sixty data points 41 are desired to plot the VSF spectrum, then at least sixty analysis units 5 must be used in the plurality. By using solid state technology to make the components of the analysis unit 5, the analysis unit 5 can be made small enough so that the plurality of analysis units 5 can be disposed within the logging instrument 10.

Figure 5:
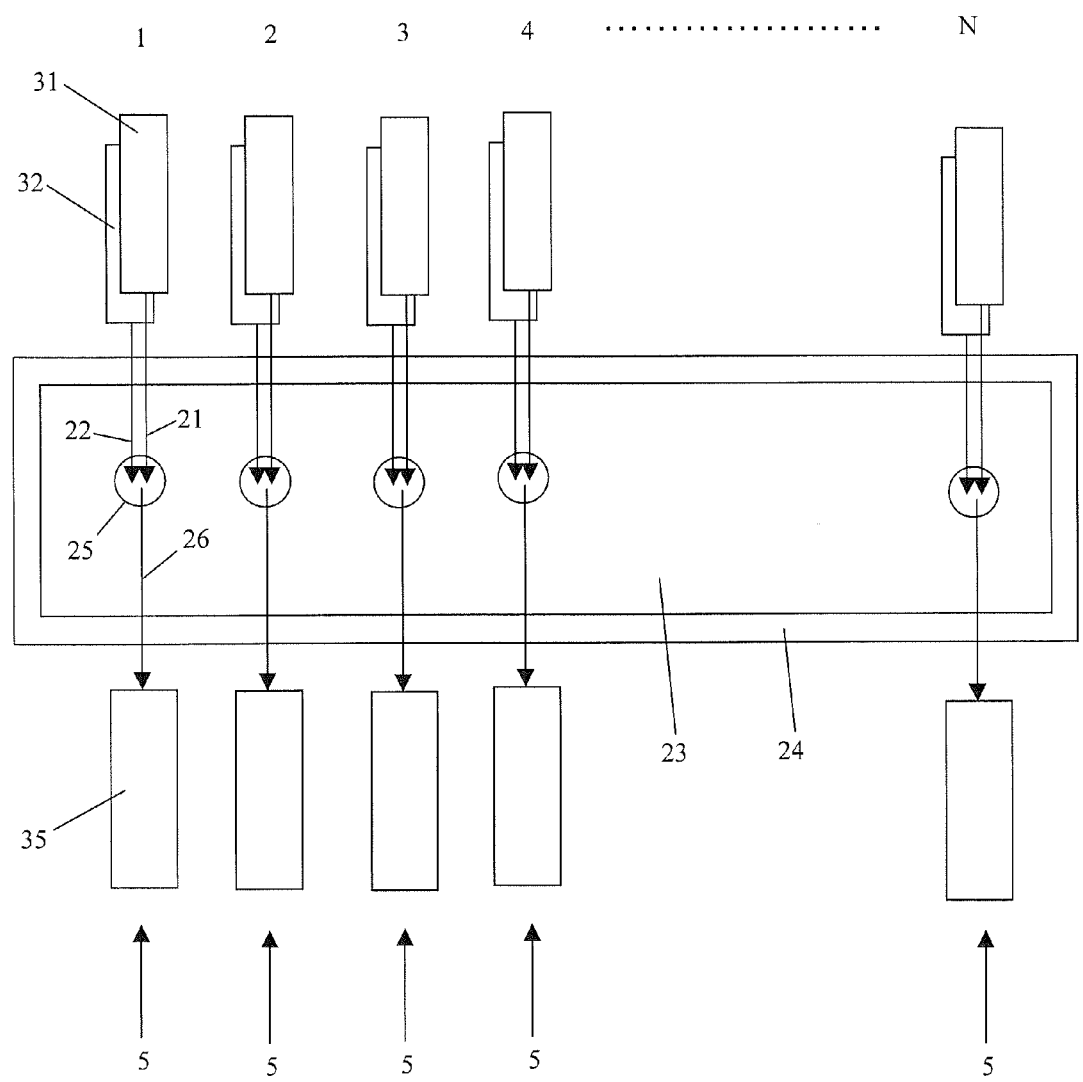
FIG. 5 illustrates an exemplary embodiment of a plurality of analysis units for performing a chemical analysis.

FIG. 5 illustrates a top view of an exemplary embodiment of an apparatus for analyzing a chemical composition of the material 23 in the borehole 2 using the plurality of the analysis units 5. Referring to FIG. 5, N analysis units 5 are included in the plurality. In the embodiment of FIG. 5, the plurality of the analysis units 5 shares a common metal surface 24.

Generally, the well logging instrument 10 includes adaptations as may be necessary to provide for operation during drilling or after a drilling process has been completed.

Figure 6:
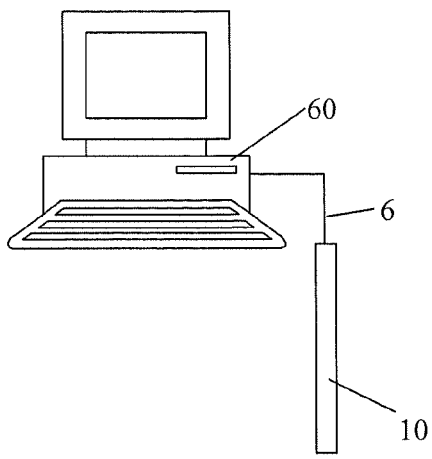
FIG. 6 illustrates an exemplary embodiment of the logging instrument connected to a computer.

Referring to FIG. 6, an apparatus for implementing the teachings herein is depicted. In FIG. 6, the apparatus includes a computer 60 coupled to the well logging instrument 10. Typically, the computer 60 includes components as necessary to provide for the real time processing of data from the well logging instrument 10. Exemplary components include, without limitation, at least one processor, storage, memory, input devices, output devices, user interfaces and the like. As these components are known to those skilled in the art, these are not depicted in any detail herein.

Generally, some of the teachings herein are reduced to an algorithm that is stored on machine-readable media. The algorithm is implemented by the computer 60 and provides operators with desired output. The output is typically generated on a real-time basis.

The logging instrument 10 may be used to provide real-time measurements for the chemical analysis. As used herein, generation of data in "real-time" is taken to mean generation of data at a rate that is useful or adequate for making decisions during or concurrent with processes such as production, experimentation, verification, and other types of surveys or uses as may be opted for by a user or operator. Accordingly, it should be recognized that "real-time" is to be taken in context, and does not necessarily indicate the instantaneous determination of data, or make any other suggestions about the temporal frequency of data collection and determination.

A high degree of quality control over the data may be realized during implementation of the teachings herein. For example, quality control may be achieved through known techniques of iterative processing and data comparison. Accordingly, it is contemplated that additional correction factors and other aspects for real-time processing may be used. Advantageously, the user may apply a desired quality control tolerance to the data, and thus draw a balance between rapidity of determination of the data and a degree of quality in the data.

Figure 7:
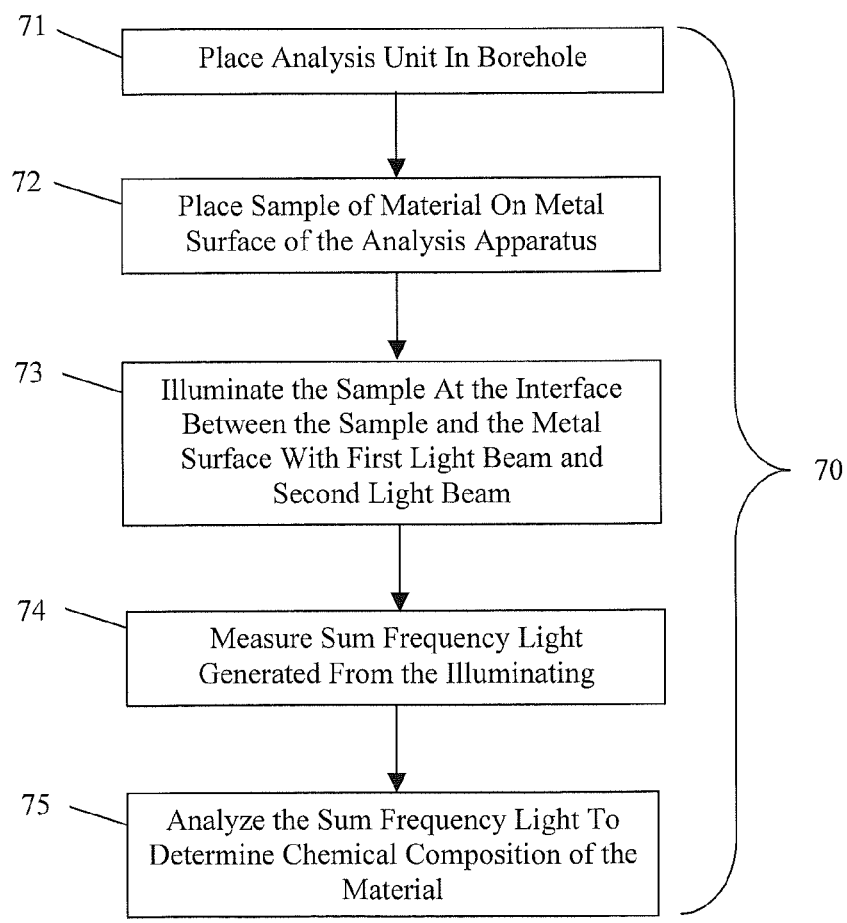
FIG. 7 presents one example of a method for analyzing a chemical composition of a material in the borehole.

FIG. 7 presents one example of a method 70 for determining a chemical composition of the material 23 in the borehole 2. The method 70 calls for placing (step 71) the analysis unit 5 in the borehole 2. Further, the method 70 calls for placing (step 72) a sample of the material 23 onto the metal surface 24 of the apparatus 5. Further, the method 70 calls for illuminating (step 73) the sample at the interface 25 between the sample and the metal surface 24 with the first light beam 21 and the second light beam 22. Further, the method 70 calls for measuring (step 74) the sum frequency light 26 generated from the illuminating. Step 74 may include measuring the intensity $I_3$ of the sum frequency light 26. Further, the method 70 calls for analyzing (step 75) the sum frequency light 26 to determine the chemical composition of the material.

Figure 8:
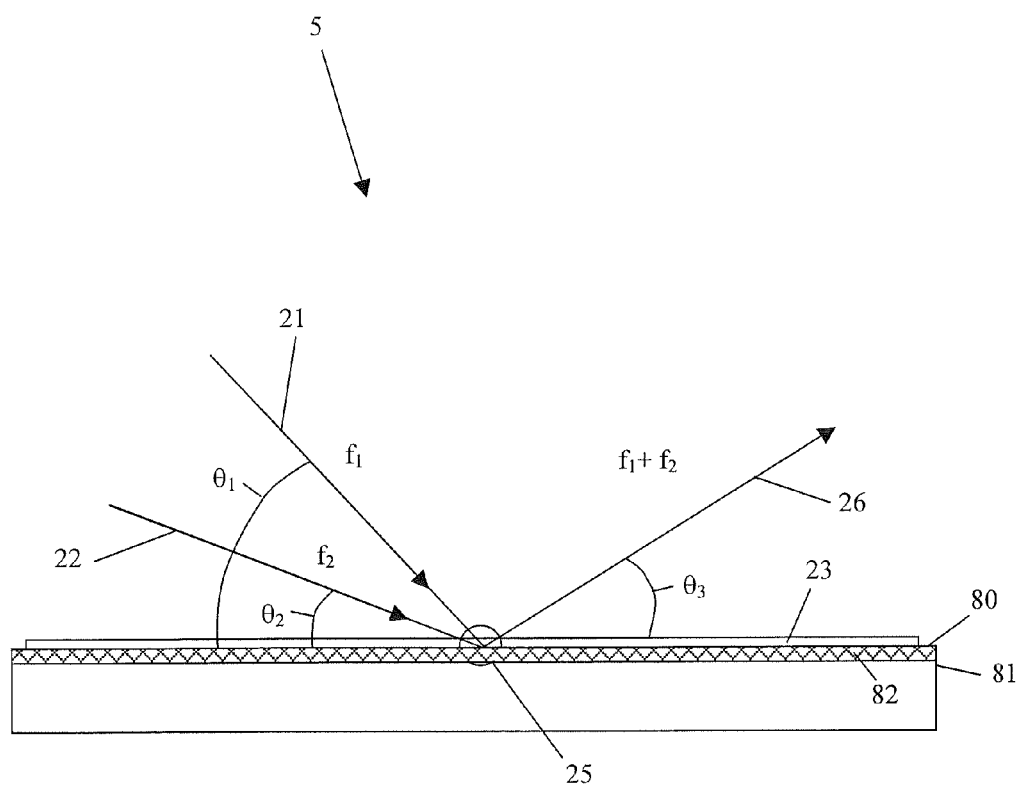
FIG. 8 illustrates an exemplary embodiment of an enhanced surface configured to perform sum-frequency spectroscopy.

In some embodiments, the intensity $I_3$ of the sum frequency light 26 from the metal surface 24 may be weak relative to noise, thus, providing a measurement with a low signal to noise ratio (SNR). To increase the intensity $I_3$ of the sum frequency light 26, an enhanced surface 80 is used at the interface 25 as shown in FIG. 8. The enhanced surface 80 is generally disposed on a support surface 81. The enhanced surface 80 includes features 82 that increase how easily atoms or molecules of the material 23 polarize at the interface 25 in response to an electric field such as the electric fields associated with the first light beam 21 or the second light beam 22. Hence, the effective second order electric susceptibility of the material 23 at the interface 25 will increase. In accordance with equation (1), increasing the second order electric susceptibility will result in increasing the intensity $I_3$ of the sum frequency light 26. By increasing the intensity $I_3$, the signal level of the sum-frequency measurement will increase resulting in an increased SNR.

Alternatively to increasing the SNR, the enhanced surface 80 can be used to increase the sensitivity of measurements. Hence, fewer molecules or atoms can be detected that might not have been detected with the conventional surface.

In one embodiment, the support surface 81 can be a substrate such as a semiconductor. Thus, the enhanced surface 80 can be fabricated on a substrate using semiconductor fabrication techniques.

The term "enhanced surface" as used herein relates to a surface having features 82 that enhance or increase nonlinear optical properties of the material 23 at the interface 25 with the enhanced surface. The nonlinear optical properties relate to the material 23 having polarization that responds nonlinearly to the electric field of light. This results in the second order electric susceptibility of the material 23 at the interface 25 being enhanced, magnified, or increased. In one embodiment, the enhanced surface can increase the second order electric susceptibility by many orders of magnitude over the second order electric susceptibility of the material 23 at an interface with a conventional surface for sum frequency spectroscopy. The conventional surface may be regarded as being a plain metal surface with no distinguishing features.

In addition to increasing the second order electric susceptibility, the enhanced surface 80 can be "functionalized" such that specific chemicals of a selected material 23 are attached to the surface 80. Therefore, the enhanced surface 80 that is functionalized can be used to discriminate between materials that are of interest and materials that are not of interest. For example, the enhanced surface 80 can be functionalized to have certain petrochemicals attach to the surface 80 for detection of a specific type while preventing other chemicals from attaching to the surface 80.

Several techniques can be used to provide the enhanced surface 80. For example, nano-structures, particles, and chemicals at the enhanced surface 80 can all individually or in combination increase the second order electric susceptibility of the material 23 at the interface 25. Non-limiting embodiments of the nano-structures include geometric structures such as cones with very small dimensions such as, in one embodiment, having a magnitude of the order of a nanometer or more. Another non-limiting nano-structure is a nanotube or nanowire. A non-limiting example of a material used in a nano-structure is carbon. Non-limiting embodiments of particles include nanoparticles. Nanoparticles range in size from on one nanometer to as much as 2500 nanometers. Non-limiting embodiments of materials for the nano-structures and particles include metals such as gold, silver and platinum. Another embodiment of the enhanced surface 80 includes nanoparticles made from a semiconductor material. Semiconductor nanoparticles are referred to as quantum dots. A quantum dot is a semiconductor in which the bound states of electron-hole pairs are confined in the three spatial dimensions. In general, a quantum dot affects light in relation to the size of the quantum dot. Thus, the size of the quantum dot can be selected to achieve a desired second order electric susceptibility. Another embodiment of the enhanced surface 80 includes quantum wires. Quantum wires are similar to quantum dots except the bound states of the electron-hole pairs are confined to two spatial dimensions allowing free propagation in the third dimension.

In general, use of the enhanced surface 80 allows one to either increase the second order electric susceptibility or to select a specific desired second order electric susceptibility of the material 24 at the interface 25.

When using the enhanced surface 80 for sum frequency spectroscopy, the method 70 can be used substituting the enhanced surface 80 for the metal surface 24.

In certain embodiments, a string of two or more logging instruments 10 may be used where each logging instrument 10 includes at least one analysis unit 5. In these embodiments, the responses from each of the analysis units 5 may be used separately or combined to produce a composite response.

In support of the teachings herein, various analysis components may be used, including digital and/or analog systems. For example, the digital and/or analog systems may be used for the electronic unit 9. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling unit, heating unit, motive force (such as a translational force, propulsional force or a rotational force), sensor, transmitter, receiver, transceiver, controller, optical unit, optical lens, electrical unit, electromechanical unit, sample pump, or sample line may be included in support of the various aspects discussed herein or in support of other functions beyond this disclosure.

The term "carrier" as used herein means any device, device component, combination of devices, media and/or member that may be used to convey, house, support or otherwise facilitate the use of another device (such as the analysis unit 5), device component, combination of devices, media and/or member. The logging instrument 10 is one non-limiting example of a carrier. Other exemplary non-limiting carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The terms "first" and "second" are used to distinguish elements and are not used to denote a particular order.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for estimating a chemical composition of a material in a borehole penetrating the earth, the method comprising:
 placing an analysis unit into the borehole;
 placing a sample of the material onto an enhanced surface of the analysis unit, the enhanced surface comprising a plurality of nano-structures configured to increase an electric susceptibility of the sample at an interface between the sample and the enhanced surface such that the electric susceptibility is greater than an electric susceptibility at an interface between the sample and a plain metal surface;
 illuminating the sample at the interface with a first light beam and a second light beam;
 measuring sum frequency light generated from the illuminating; and
 analyzing the sum frequency light to estimate the chemical composition of the material.

2. The method of claim 1, wherein the electric susceptibility is second order electric susceptibility.

3. The method of claim 1, wherein each nano-structure comprises a shape of at least one of a cone, a tube, and a wire.

4. The method of claim 1, wherein each nano-structure comprises carbon.

5. The method of claim 1, wherein the plurality of nano-structures comprises nanoparticles.

6. The method of claim 5, wherein each nanoparticle comprises at least one of gold, silver, and platinum.

7. The method of claim 1, wherein the plurality of nano-structures comprises at least one of quantum dots and quantum wires.

8. The method of claim 1, wherein the nano-structures are arranged in an ordered array.

9. The method of claim 8, further comprising selecting the order to achieve a selected second order dielectric susceptibility.

10. The method of claim 1, further comprising selecting a size of the nano-structures to achieve a selected second order dielectric susceptibility.

11. The method of claim 1, wherein measuring comprises measuring an intensity of the sum frequency generated light.

12. The method of claim 1, wherein the material comprises a petroleum compound.

13. The method of claim 1, further comprising varying the frequency of the first light beam in the infrared region of the light spectrum while keeping constant the frequency of the second light beam in the visible region of the light spectrum.

14. The method of claim 13, further comprising developing a vibrational sum frequency (VSF) spectrum for the material from the varying.

15. The method of claim 14, wherein analyzing comprises comparing the VSF spectrum to a reference VSF spectrum to determine the chemical composition of the material.

16. A non-transitory computer readable medium comprising machine executable instructions for estimating a chemical composition of a material in a borehole penetrating the earth by performing a method comprising:
 placing an analysis unit into the borehole;
 placing a sample of the material onto an enhanced surface of the analysis unit, the enhanced surface comprising a plurality of nano-structures configured to increase the electric susceptibility of the sample at an interface between the sample and the enhanced surface such that the electric susceptibility is greater than an electric susceptibility at an interface between the sample and a plain metal surface;
 illuminating the sample at the interface with a first light beam and a second light beam;
 measuring sum frequency light generated from the illuminating; and
 analyzing the sum frequency light to estimate the chemical composition of the material.

17. An apparatus for estimating a chemical composition of a material in a borehole penetrating the earth, the apparatus comprising:
 a carrier; and
 an analysis unit disposed at the carrier, the analysis unit comprising an enhanced surface, a first light source and a second light source, and a light detector, the enhanced surface comprising a plurality of nano-structures configured to increase an electric susceptibility of the sample at an interface between the sample and the enhanced surface such that the electric susceptibility is greater than an electric susceptibility at an interface between the sample and a plain metal surface;
 wherein the analysis unit is configured to receive a sample of the material from a downhole environment onto the enhanced surface, illuminate the material at the interface with the light sources, and measure a characteristic of sum frequency light generated from the illumination with the light detector to estimate the chemical composition.

18. The apparatus of claim 17, wherein the enhanced surface is further configured to attach to a specific chemical.

19. The apparatus of claim 18, wherein the enhanced surface is further configured to prevent a specific chemical from attaching to the enhanced surface.

20. The apparatus of claim 17, wherein at least one of the light sources comprises a filter for providing light at at least one of a desired frequency and a desired polarization.

21. The apparatus of claim 17, further comprising an iris for spatially filtering light emitted from the material at the interface.

22. The apparatus of claim 17, wherein the carrier is configured to traverse the borehole by at least one of a wireline, a slickline, coiled tubing, and a drill string.

* * * * *